(12) United States Patent
Cho et al.

(10) Patent No.: US 12,319,729 B1
(45) Date of Patent: Jun. 3, 2025

(54) **ANTI-*STAPHYLOCOCCUS AUREUS* SPECIFIC ANTIBODY AND NUCLEIC ACID ENCODING SEQUENCE THEREOF, AND USES OF THE SAME**

(71) Applicant: China Medical University Hospital, Taichung (TW)

(72) Inventors: Der-Yang Cho, Taichung (TW); Shao-Chih Chiu, Taichung (TW); Shi-Wei Huang, Taichung (TW); Chih-Ming Pan, Taichung (TW); Mei-Chih Chen, Taichung (TW); Yeh Chen, Taichung (TW); Po-Ren Hsueh, Taichung (TW); Tien Ni, Taichung (TW); Jia-Xin Yu, Taichung (TW); Chao-Jung Chen, Taichung (TW)

(73) Assignee: CHINA MEDICAL UNIVERSITY HOSPITAL, Taichung (TW)

( * ) Notice: Subject to any disclaimer, the term of this patent is extended or adjusted under 35 U.S.C. 154(b) by 0 days.

(21) Appl. No.: 18/624,353

(22) Filed: Apr. 2, 2024

(51) Int. Cl.
C07K 16/12 (2006.01)
A61K 39/00 (2006.01)
A61P 31/04 (2006.01)

(52) U.S. Cl.
CPC .......... *C07K 16/1271* (2013.01); *A61P 31/04* (2018.01); *A61K 2039/505* (2013.01); *C07K 2317/565* (2013.01)

(58) Field of Classification Search
CPC .......... C07K 16/1271; C07K 2317/565; C07K 2317/92; A61P 31/04; A61K 2039/505
See application file for complete search history.

(56) References Cited

PUBLICATIONS

Rudikoff et al. "Single amino acid substitution altering antigen-binding specificity", Mar. 1982, Proceedings of the National Academies of Sciences, vol. 79, p. 1979-1983. (Year: 1982).*
MacCallum et al. "Antibody-antigen Interactions: Contact Analysis and Binding Site Topography", 1996, Journal of Molecular Biology, vol. 262, p. 732-745. (Year: 1996).*
Pascalis et al. "Grafting of "Abbreviated" Complementarity-Determining Regions Containing Specificity-Determining Residues Essential for Ligand Contact to Engineer a Less Immunogenic Humanized Monoclonal Antibody", 2002, The Journal of Immunology, p. 3076-3084 (Year: 2002).*
Casset et al. "A peptide mimetic of an anti-CD4 monoclonal antibody by rational design" 2003, Biochemical and Biophysical Research Communications, vol. 307, p. 198-205. (Year: 2003).*
Vajdos et al. "Comprehensive Functional Maps of the Antigen-binding Site of an Anti-ErbB2 Antibody Obtained with Shotgun Scanning Mutagenesis", 2002, Journal of Molecular Biology, vol. 320, p. 415-428. (Year: 2002).*

(Continued)

*Primary Examiner* — Gary B Nickol
*Assistant Examiner* — Bailey M Morgan
(74) *Attorney, Agent, or Firm* — WPAT, PC

(57) ABSTRACT

The present disclosure provides an anti-*Staphylococcus aureus* specific antibody and the nucleic acid encoding sequence thereof, and uses of the same. The anti-*Staphylococcus aureus* specific antibody of the present disclosure achieves the effect of treating *Staphylococcus aureus* infection and enhancing immune cells against *Staphylococcus aureus* through various efficacy experiments.

9 Claims, 4 Drawing Sheets

Specification includes a Sequence Listing.

(56) References Cited

PUBLICATIONS

"AI-Based Biomarker Screening Accelerates Drug Development Against Superbugs", Sep. 26, 2024, Healthcare B2B. Obtained online at taiwan-healthcare.org [retrieved on Nov. 14, 2024]. Retrieved from the Internet: <taiwan-healthcare.org/en/news-detail?id=0skffed4oupehk09> (Year: 2024).*

* cited by examiner

SEQUENCE LISTING

```
Sequence total quantity: 12
SEQ ID NO: 1            moltype = AA  length = 9
FEATURE                 Location/Qualifiers
source                  1..9
                        mol_type = protein
                        organism = synthetic construct
SEQUENCE: 1
AGSISYSNA                                                                9

SEQ ID NO: 2            moltype = AA  length = 8
FEATURE                 Location/Qualifiers
source                  1..8
                        mol_type = protein
                        organism = synthetic construct
SEQUENCE: 2
KISYSGAY                                                                 8

SEQ ID NO: 3            moltype = AA  length = 11
FEATURE                 Location/Qualifiers
source                  1..11
```

-continued

```
                        mol_type = protein
                        organism = synthetic construct
SEQUENCE: 3
IMYRGTLEFQ F                                                              11

SEQ ID NO: 4            moltype = AA   length = 11
FEATURE                 Location/Qualifiers
source                  1..11
                        mol_type = protein
                        organism = synthetic construct
SEQUENCE: 4
RASENLDNLL N                                                              11

SEQ ID NO: 5            moltype = AA   length = 7
FEATURE                 Location/Qualifiers
source                  1..7
                        mol_type = protein
                        organism = synthetic construct
SEQUENCE: 5
YTTSLDS                                                                    7

SEQ ID NO: 6            moltype = AA   length = 9
FEATURE                 Location/Qualifiers
source                  1..9
                        mol_type = protein
                        organism = synthetic construct
SEQUENCE: 6
QQANYRTIT                                                                  9

SEQ ID NO: 7            moltype = AA   length = 123
FEATURE                 Location/Qualifiers
source                  1..123
                        mol_type = protein
                        organism = synthetic construct
SEQUENCE: 7
QVQLVQSGAE  VKKPGASVKV  SCKASAGSIS  YSNAAMHWVR  QAPGQGLEWM  GAIKISYSGA     60
YASYNQKFKG  RVTITAVTSA  STAYMELSSL  RSEDTAVYYC  ARIMYRGTLE  FQFWGQGTLV    120
TVS                                                                      123

SEQ ID NO: 8            moltype = AA   length = 107
FEATURE                 Location/Qualifiers
source                  1..107
                        mol_type = protein
                        organism = synthetic construct
SEQUENCE: 8
DIQMTQSPSS  LSASVGDRVT  ITCRASENLD  NLLNWLQQKP  GKAIKRLIYY  TTSLDSGVPK     60
RFSGSRSGSD  YSLTISSLQP  EDFATYYCQQ  ANYRTITFGQ  GTKLEIK                  107

SEQ ID NO: 9            moltype = DNA   length = 369
FEATURE                 Location/Qualifiers
source                  1..369
                        mol_type = other DNA
                        organism = synthetic construct
SEQUENCE: 9
caggtgcagc  tggtgcagag  cggcgccgag  gtgaaaaagc  ctggagcttc  tgtgaaggtg     60
agctgcaagg  ccagcgccgg  cagcatcagc  tacagcaatg  ctgccatgca  ctgggttagg    120
caggcccctg  gccagggact  tgaatggatg  ggcgctatca  agatcagcta  cagcggcgcc    180
tacgccagct  acaaccagaa  gttcaagggc  agggtgacca  tcaccgccgt  gaccagcgct    240
tctacagcct  acatggagct  gagcagcctg  aggagcgagg  acaccgccgt  gtactattgc    300
gctaggatca  tgtacagggg  caccctggag  ttccagttct  ggggccaggg  cacccttgtt    360
acagtgagc                                                                369

SEQ ID NO: 10           moltype = DNA   length = 321
FEATURE                 Location/Qualifiers
source                  1..321
                        mol_type = other DNA
                        organism = synthetic construct
SEQUENCE: 10
gacatccaga  tgacccagag  ccccagcagc  ctgagcgcct  ctgttggaga  tagggtgacc     60
atcacctgta  gggccagcga  gaacctggac  aacctgctga  actggctgca  gcagaagccc    120
ggcaaggcca  tcaagaggct  gatctactac  accaccagcc  tggacagcgg  cgtgcccaag    180
aggtttagcg  gctctaggtc  tggaagcgac  tacagcctga  ccatcagcag  cctgcagccc    240
gaggacttcg  ctacctacta  ctgccagcag  gccaactaca  ggaccatcac  cttcggccag    300
ggcaccaagc  tggagatcaa  g                                                321

SEQ ID NO: 11           moltype = AA   length = 59
FEATURE                 Location/Qualifiers
source                  1..59
                        mol_type = protein
```

```
                       organism = Staphylococcus aureus
SEQUENCE: 11
ADESKFDQFK GNVKETVGNV TDNKELEKEG QQDKATGKAK EVVENAKNKI TDAIDKLKK    59

SEQ ID NO: 12          moltype = AA   length = 59
FEATURE                Location/Qualifiers
source                 1..59
                       mol_type = protein
                       organism = Staphylococcus aureus
SEQUENCE: 12
ADESKFDQFK GNVKETVGNV TDNKELEKEG QQDKVIGKAK EVVENAKNKI TDAIDKLKK    59
```

ANTI-*STAPHYLOCOCCUS AUREUS* SPECIFIC ANTIBODY AND NUCLEIC ACID ENCODING SEQUENCE THEREOF, AND USES OF THE SAME

STATEMENT REGARDING SEQUENCE LISTING

The sequence listing associated with this application is provided in text format in lieu of a paper copy and is hereby incorporated by reference into the specification. The name of the XML file containing the sequence listing is 113F0073-IE_Sequence_listing. The XML file is 13000 bytes; was created on Mar. 29, 2024.

BACKGROUND OF THE INVENTION

1. Field of the Invention

The present invention relates to an anti-*Staphylococcus aureus* specific antibody and the nucleic acid encoding sequence thereof, and uses of the same.

2. The Prior Art

*Staphylococcus aureus* is a Gram-positive, facultative aerobe that often colonizes the skin and nose of healthy individuals. This bacterium is considered an opportunistic pathogen and can cause a variety of diseases/conditions in many body parts. It is a leading cause of bloodstream, skin and soft tissue, and respiratory tract infections worldwide. The frequency of health care and community-associated infections caused by *Staphylococcus aureus* has increased. Efforts to combat these infections are hampered by the emergence of drug-resistant strains, especially Methicillin-resistant *Staphylococcus aureus* (MRSA) strains.

*Staphylococcus aureus* exhibits many virulence factors (cell surface expression and secretion) that promote bacterial invasion and dissemination in the host. Most of the secreted virulence factors are toxins, the most prominent of which is the pore-forming toxin hemolysin A. *Staphylococcus aureus* hemolysin A is a 33 kDa secreted monomer that oligomerizes into a heptameric structure in the host cell membrane to form pores, leading to cell lysis, epithelial barrier disruption, inflammation, and tissue damage.

In view of the fact that the current drugs for treating *Staphylococcus aureus* infection still have the shortcomings of side effects, cytotoxicity, chemical synthesis and ineffectiveness. In order to solve the above-mentioned problems, those skilled in the art urgently need to develop a novel and effective medicament for treating *Staphylococcus aureus* infection and enhancing immune cells against *Staphylococcus aureus* for the benefit of a large group of people in need thereof.

SUMMARY OF THE INVENTION

A primary objective of the present invention is to provide an anti-*Staphylococcus aureus* specific antibody, comprising an amino acid sequence of SEQ ID NO:1-SEQ ID NO:6.

Another objective of the present invention is to provide an isolated nucleic acid, encoding the amino acid sequence of the aforementioned anti-*Staphylococcus aureus* specific antibody.

Another objective of the present invention is to provide a pharmaceutical composition, comprising the aforementioned anti-*Staphylococcus aureus* specific antibody and a pharmaceutically acceptable carrier.

Another objective of the present invention is to provide a method for treating *Staphylococcus aureus* infection and enhancing immune cells against *Staphylococcus aureus*, comprising administering to a subject in need thereof the aforementioned pharmaceutical composition.

According to an embodiment of the present invention, the amino acid sequence of SEQ ID NO:1-SEQ ID NO:6 is complementarity determining region (CDR).

According to an embodiment of the present invention, the amino acid sequence of SEQ ID NO:1 and SEQ ID NO:4 is CDR1, the amino acid sequence of SEQ ID NO:2 and SEQ ID NO:5 is CDR2, and the amino acid sequence of SEQ ID NO:3 and SEQ ID NO:6 is CDR3.

According to an embodiment of the present invention, the anti-*Staphylococcus aureus* specific antibody specifically binds to a mutant recombinant *Staphylococcus aureus* UPF0337 protein SA1452.

According to an embodiment of the present invention, the anti-*Staphylococcus aureus* specific antibody consists of an amino acid sequence of SEQ ID NO:7 and SEQ ID NO:8, wherein the amino acid sequence of SEQ ID NO:7 is heavy chain variable domain (VH), the amino acid sequence of SEQ ID NO:8 is light chain variable domain (VL), the amino acid sequence of SEQ ID NO:1-SEQ ID NO:3 is located on the VH, and the amino acid sequence of SEQ ID NO:4-SEQ ID NO:6 is located on the VL.

According to an embodiment of the present invention, the anti-*Staphylococcus aureus* specific antibody is in an antibody form selected from the group consisting of: single-chain variable fragment (scFv), minibody, nanobody, monoclonal antibody, immunoglobulin G (IgG), immunoglobulin A (IgA), and conjugated form.

According to an embodiment of the present invention, the isolated nucleic acid consists of nucleotide sequence of SEQ ID NO:9 and SEQ ID NO:10.

According to an embodiment of the present invention, the *Staphylococcus aureus* is Methicillin-resistant *Staphylococcus aureus* (MRSA).

In summary, the anti-*Staphylococcus aureus* specific antibody of the present invention has the effects on treating MRSA infection, directly combating MRSA, and enhancing the efficacy of immune cells against MRSA through the experiments illustrated in the following examples.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

(FIG. 2B) SA1452 mAb significantly prevents death in mice with MRSA bacteremia. (FIGS. 2C and 2D) The lungs, livers and kidneys of mice treated with SA1452 mAb were homogeneously extracted with PBS. One day after the tissue extract (50 mg) was inoculated into BP agar plates, the number of MRSA colonies formed was significantly less than that of the control group, indicating that SA1452 mAb has excellent effect on treating MRSA infection.

DETAILED DESCRIPTION OF THE PREFERRED EMBODIMENT

Figure 1A:
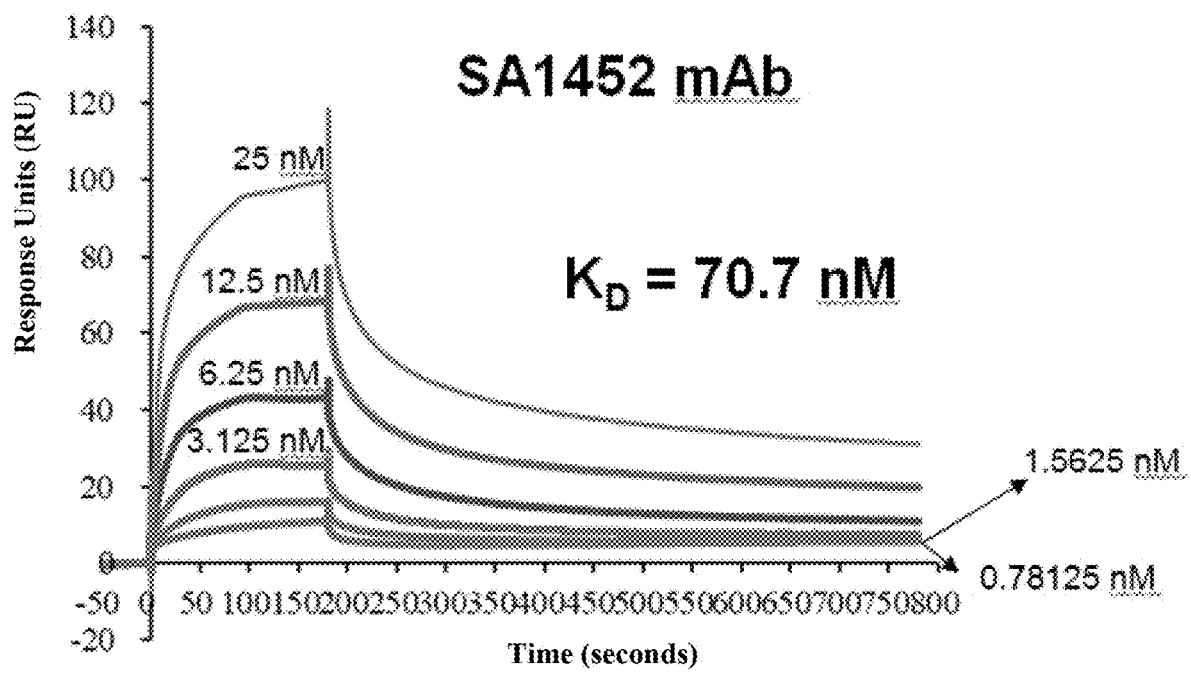
FIGS. 1A-1C show SPR analysis for binding affinity of the anti-*Staphylococcus aureus* specific antibody (SA1452 mAb), in which the affinity KD of SA1452 mAb to SA1452 recombinant protein is found to be 70.7 nM (FIG. 1A); Methicillin-resistant *Staphylococcus aureus* (MRSA) ($1 \times 10^6$ CFU in 150 ml in BP broth, triplicate) was treated with or without SA1452 mAb (0, 0.1, 0.5, 1, 5, 10 µg/ml) for 1, 2, 4, 6, 8, 24 and 48 h, at the indicated time points, the growth of MRSA was measured by enzyme-linked immunosorbent assay (ELISA) reader through O.D. 600 nm channel (FIG. 1B); MRSA ($1 \times 10^6$ CFU) was added into whole blood (1 ml) and presence with or without SA1452 mAb (0, 0.5 or 1 µg/ml) for 2 h, then the serum was collected, 10 ml serum was performed to seed on the BP agar plate, after 24 h, the colonies were recorded; it was found in FIG. 1C that SA1452 mAb can assist blood cells in resisting MRSA colony formation.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of 20%, preferably within +10%, and most preferably within 5%.

Unless otherwise stated in the context, "a", "the" and similar terms used in the specification (especially in the following claims) should be understood as including singular and plural forms.

As used herein, the term "treating" or "treatment" refers to alleviating, reducing, ameliorating, relieving or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of intraperitoneal injection, subcutaneous injection, intraepidermal injection, intradermal injection, intramuscular injection, intravenous injection, and intralesional injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

As used herein, the term "nucleic acid", "nucleic acid sequence" or "nucleic acid fragment" refers to a sequence of deoxyribonucleotides or ribonucleotides in single- or double-stranded forms, and comprises known naturally occurring nucleotides or artificially chemical mimics. As used herein, the term "nucleic acid" is used interchangeably with the terms "gene", "cDNA", "mRNA", "oligonucleotide" and "polynucleotide".

In this example, the anti-*Staphylococcus aureus* specific antibody of the present invention can comprise an amino acid sequence of SEQ ID NO:1-SEQ ID NO:6, wherein the amino acid sequence of SEQ ID NO:1-SEQ ID NO:6 is complementarity determining region (CDR), the amino acid sequence of SEQ ID NO:1 is CDR1, the amino acid sequence of SEQ ID NO:2 is CDR2, the amino acid sequence of SEQ ID NO:3 is CDR3, the amino acid sequence of SEQ ID NO:4 is CDR4, the amino acid sequence of SEQ ID NO:5 is CDR5, and the amino acid sequence of SEQ ID NO:6 is CDR6.

In this example, the anti-*Staphylococcus aureus* specific antibody of the present invention can comprise an amino acid sequence of SEQ ID NO:7 and SEQ ID NO:8, wherein the amino acid sequence of SEQ ID NO:7 is heavy chain variable domain (VH), and the amino acid sequence of SEQ ID NO:8 is light chain variable domain (VL).

In this example, the amino acid sequence of SEQ ID NO:1-SEQ ID NO:3 is also located on the VH, and the amino acid sequence of SEQ ID NO:4-SEQ ID NO:6 is also located on the VL.

In this example, the nucleotide sequence encoding the amino acid sequence of the VH of the anti-*Staphylococcus aureus* specific antibody is SEQ ID NO:9, and the nucleotide sequence encoding the amino acid sequence of the VL of the anti-*Staphylococcus aureus* specific antibody is SEQ ID NO: 10.

In this example, the anti-*Staphylococcus aureus* specific antibody of the present invention can specifically bind to a mutant recombinant *Staphylococcus aureus* UPF0337 protein SA1452, wherein the amino acid sequence of wild type UPF0337 protein SA1452 is SEQ ID NO:11, and the amino acid sequence of mutant UPF0337 protein SA1452 is SEQ ID NO: 12.

Example 1

Preparation of Anti-*Staphylococcus aureus* Specific Antibody of Present Invention In this example, the preparation process of the anti-*Staphylococcus aureus* specific antibody (hereinafter referred to as SA1452 mAb) is as follows. HEK293 cells (2×10⁶ cell/mL, total 200 ml) were transfected with 400 mg SA1452 mAb-expressing pcDNA3.1 vector by using PEI-MAX transfection reagent (FISHER SCIENTIFIC®) in 12 ml volume according to user instruction. After 72 h incubation, the medium will be refreshed with 200 ml complete media. At the 7$^{th}$ days post transfection, all supernatants were collected, then centrifuge at 10,000 rpm for 10 min to collect the supernatant. After purification with protein A, SA1452 mAb was purified by HPLC at the ~150 kDa protein extractions.

Example 2

Surface Plasmon Resonance (SPR) Analysis for Binding Affinity of SA1452 mAb of Present Invention In this example, the experimental procedure of the surface plasmon resonance (SPR) analysis for binding affinity of SA1452 mAb is as follows. The NTA chip, research grade will be performed for SPR analysis by BIACORE® T200 (BIACORE®-GE Healthcare, Piscataway, NJ). Briefly, dilute protein (SA1452 recombinant protein) sample in the 10 mM buffer solutions (pH 4.0, 5.5 or 6.0) at the concentration range of 20 µg/mL to give maximum surface retention for immobilization on the chip, following the SURFACE PREPARATION process and choosing the condition of higher surface concentration of ligands (SA1452 mAb: 25, 12.5, 6.25, 3.125, 1.5625 and 0.78125 nM) on the chip. Then the regeneration scouting and surface performance test, following REGENERATION SCOUTING and SURPACE PERFORMANCE TEST and then select REGENERATION METHOD to run the experiment. And then select BINDING ANALYSIS and DIRECT BINDING to investigate protein binding. The KINETIC ANALYSIS will be selected and choose MASS TRANSFER to run kinetic assay accompany with binding experiment. Data analysis and kinetic constants determine.

Figure 1B:
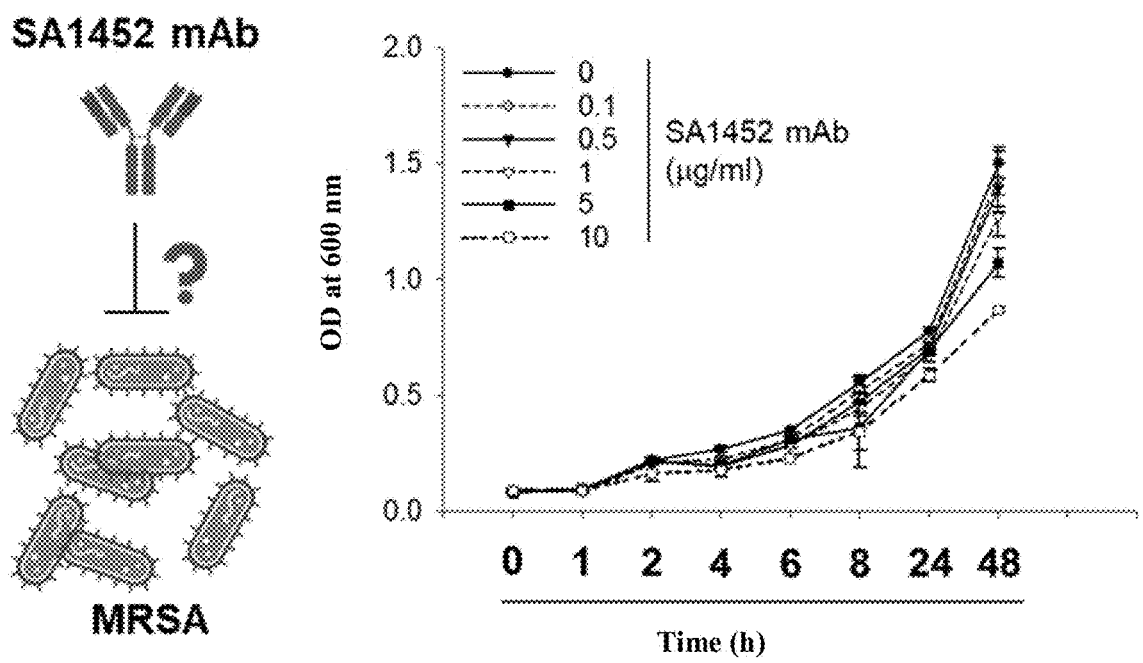
Figure 1C:
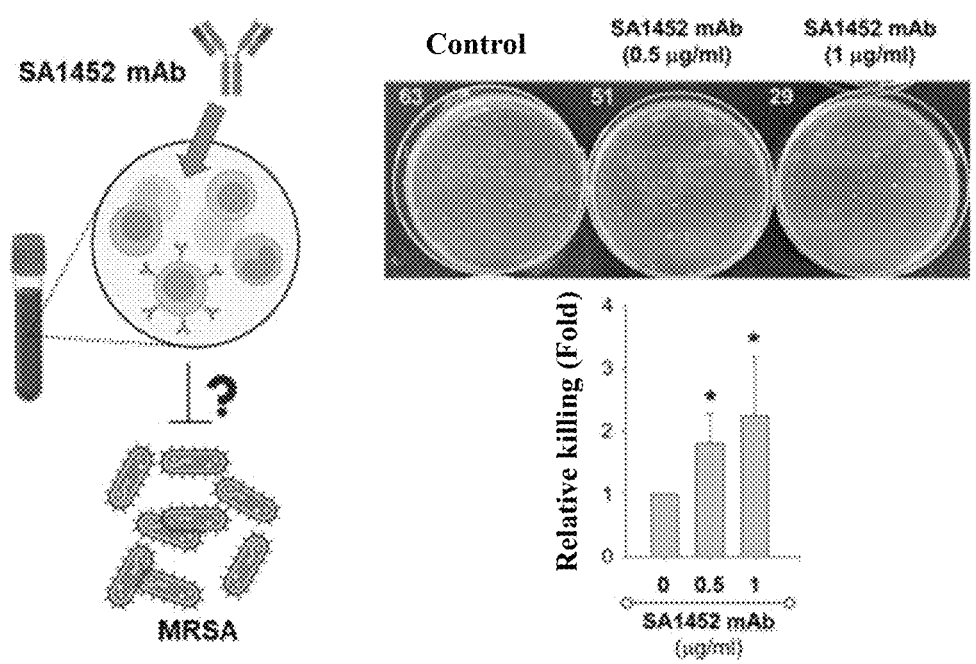
Figure 2A:
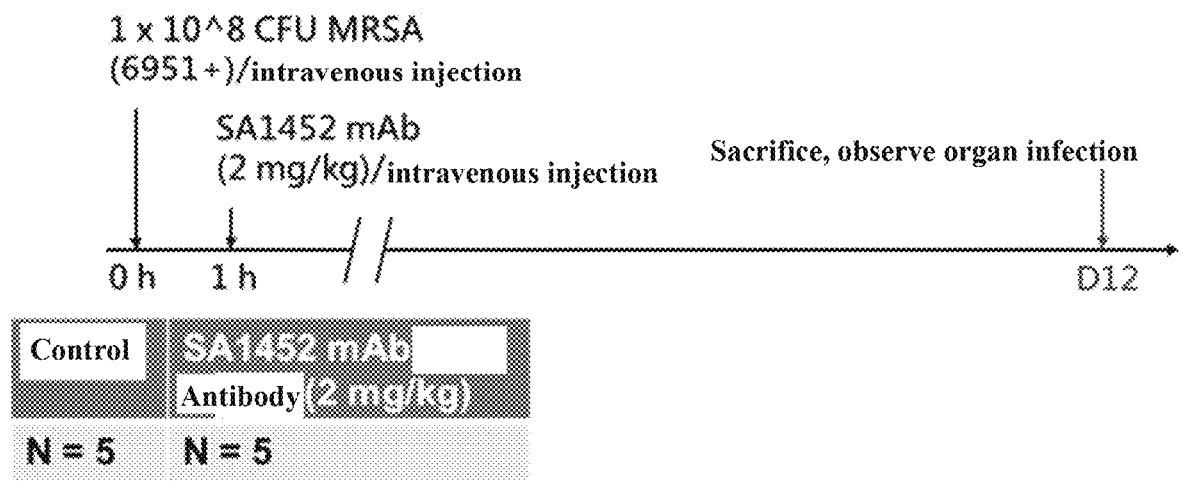
FIGS. 2A-2D show the effectiveness of SA1452 mAb on treating MRSA infection, in which (FIG. 2A) bacteremia mouse model experimental flow chart. C57BL/6 mice (N=5) were injected into the tail vein with $1\times10^8$ CFU of MRSA/per mouse. One hour later, 2 mg/kg of SA1452 mAb or saline was injected into the tail vein. The survival rate was then observed and monitored; or mice were sacrificed on the 12th day, and lung, liver and kidney tissues were taken for MRSA colony formation analysis to measure the degree of MRSA infection in the lungs, liver and kidneys.
Figure 2B:
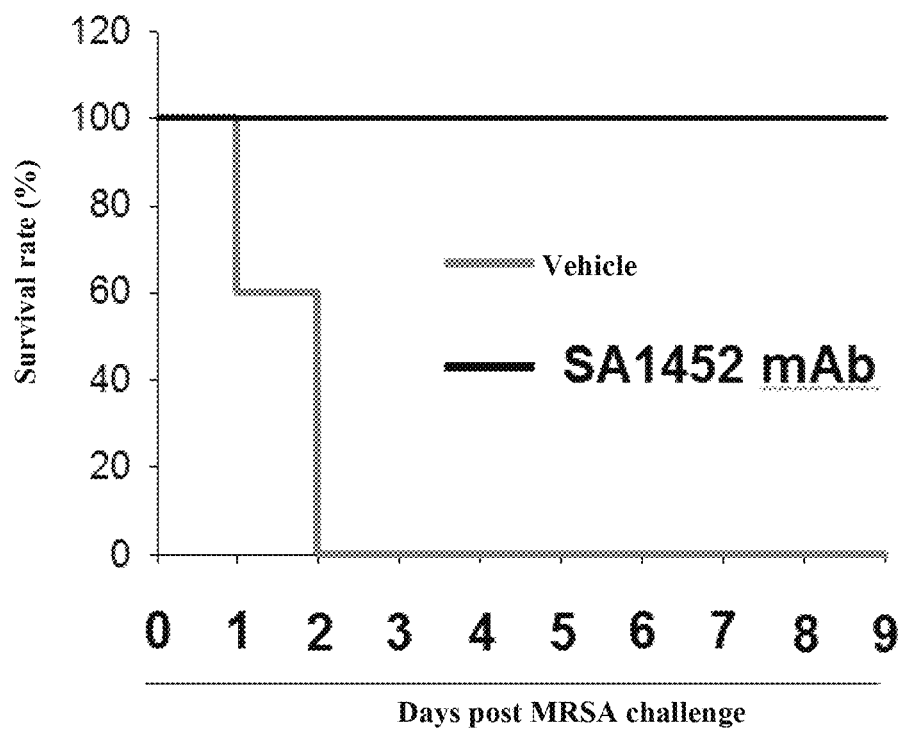
Figure 2C:
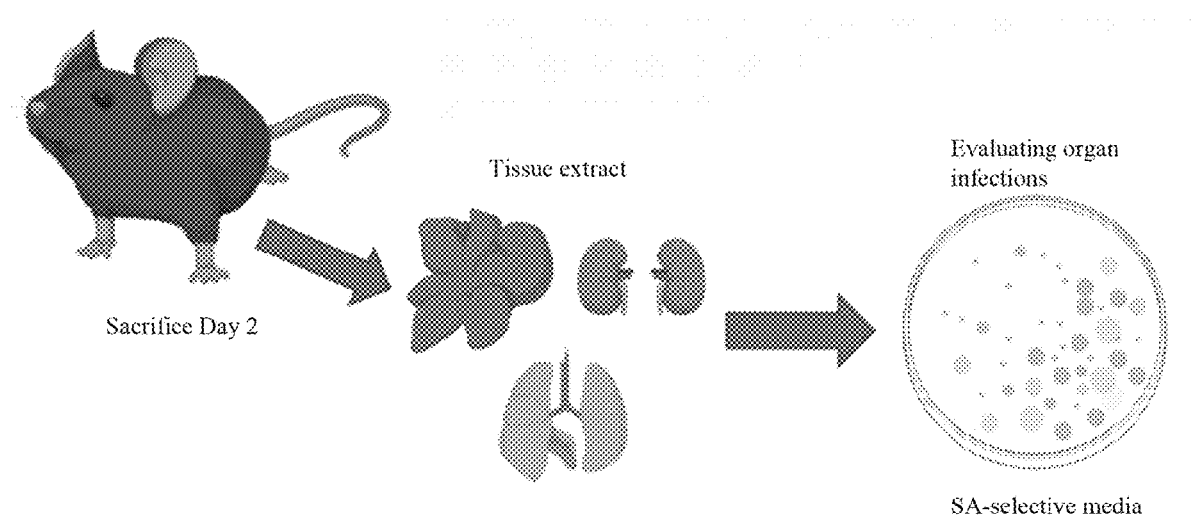
Figure 2D:
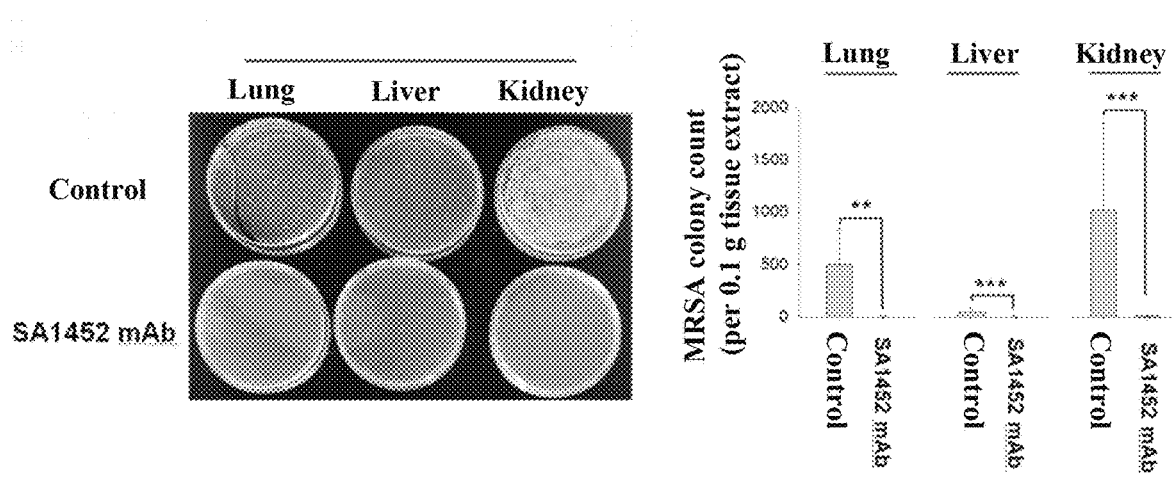

FIGS. 1A-1C show SPR analysis for binding affinity of the anti-*Staphylococcus aureus* specific antibody (SA1452 mAb), in which the affinity KD of SA1452 mAb to SA1452 recombinant protein is found to be 70.7 nM (FIG. 1A); Methicillin-resistant *Staphylococcus aureus* (MRSA) (1×10⁶ CFU in 150 ml in BP broth, triplicate) was treated with or without SA1452 mAb (0, 0.1, 0.5, 1, 5, 10 mg/ml) for 1, 2, 4, 6, 8, 24 and 48 h, at the indicated time points, the growth of MRSA was measured by enzyme-linked immunosorbent assay (ELISA) reader through O.D. 600 nm channel (FIG. 1B); MRSA (1×10⁶ CFU) was added into whole blood (1 ml) and presence with or without SA1452 mAb (0, 0.5 or 1 mg/ml) for 2 h, then the serum was collected, 10 ml serum was performed to seed on the BP agar plate, after 24 h, the colonies were recorded; it was found in FIG. 1C that SA1452 mAb can assist blood cells in resisting MRSA colony formation.

As shown in FIGS. 1A-1C, SA1452 mAb directly combats MRSA and enhances immune cells against MRSA.

Example 3

Evaluation of Effectiveness of SA1452 mAb of Present Invention on Treating MRSA Infection The effectiveness of the SA1452 mAb of the present invention on treating MRSA infection is evaluated in this example.

FIGS. 2A-2D show the effectiveness of SA1452 mAb on treating MRSA infection, in which (FIG. 2A) bacteremia mouse model experimental flow chart. C57BL/6 mice (N=5) were injected into the tail vein with 1×10⁸ CFU of MRSA/ per mouse. One hour later, 2 mg/kg of SA1452 mAb or saline was injected into the tail vein. The survival rate was then observed and monitored; or mice were sacrificed on the 12th day, and lung, liver and kidney tissues were taken for MRSA colony formation analysis to measure the degree of MRSA infection in the lungs, liver and kidneys. (FIG. 2B) SA1452 mAb significantly prevents death in mice with MRSA bacteremia. (FIGS. 2C and 2D) The lungs, livers and kidneys of mice treated with SA1452 mAb were homogeneously extracted with PBS. One day after the tissue extract (50 mg) was inoculated into BP agar plates, the number of MRSA colonies formed was significantly less than that of the control group, indicating that SA1452 mAb has excellent effect on treating MRSA infection.

In summary, the anti-*Staphylococcus aureus* specific antibody of the present invention has the effects on treating MRSA infection, directly combating MRSA, and enhancing the efficacy of immune cells against MRSA through the experiments illustrated in the above mentioned examples.

Although the present invention has been described with reference to the preferred embodiments, it will be apparent to those skilled in the art that a variety of modifications and changes in form and detail may be made without departing from the scope of the present invention defined by the appended claims.

What is claimed is:

1. An anti-*Staphylococcus aureus* specific antibody, comprising each of amino acid sequences of SEQ ID NO:7 and SEQ ID NO: 8, wherein the amino acid sequence of SEQ ID NO:7 is a heavy chain variable domain (VH), the amino acid sequence of SEQ ID NO:8 is a light chain variable domain (VL).

2. The anti-*Staphylococcus aureus* specific antibody according to claim 1, which specifically binds to a mutant recombinant *Staphylococcus aureus* UPF0337 protein SA1452.

3. The anti-*Staphylococcus aureus* specific antibody according to claim 1, which is in an antibody form selected from the group consisting of: single-chain variable fragment (scFv), minibody, monoclonal antibody, immunoglobulin G (IgG), immunoglobulin A (IgA), and conjugated forms thereof.

4. A pharmaceutical composition, comprising the anti-*Staphylococcus aureus* specific antibody according to claim 1 and a pharmaceutically acceptable carrier.

5. The pharmaceutical composition according to claim 4, wherein the anti-*Staphylococcus aureus* specific antibody specifically binds to a mutant recombinant *Staphylococcus aureus* UPF0337 protein SA1452.

6. The pharmaceutical composition according to claim 4, wherein the anti-*Staphylococcus aureus* specific antibody is in an antibody form selected from the group consisting of: single-chain variable fragment (scFv), minibody, monoclonal antibody, immunoglobulin G (IgG), immunoglobulin A (IgA), and conjugated forms thereof.

7. A method for treating *Staphylococcus aureus* infection and enhancing immune cells against *Staphylococcus aureus*, comprising administering to a subject in need thereof the pharmaceutical composition according to claim 4.

8. The method according to claim 7, wherein the anti-*Staphylococcus aureus* specific antibody specifically binds to a mutant recombinant *Staphylococcus aureus* UPF0337 protein SA1452.

9. The method according to claim 7, wherein the *Staphylococcus aureus* is Methicillin-resistant *Staphylococcus aureus* (MRSA).

\* \* \* \* \*